United States Patent
Britz et al.

(10) Patent No.: US 7,476,514 B2
(45) Date of Patent: Jan. 13, 2009

(54) METHOD FOR MONITORING THE IMMUNE RESPONSE AND PREDICTING CLINICAL OUTCOMES IN TRANSPLANT RECIPIENTS

(75) Inventors: Judith A. Britz, Laurel, MD (US); Peter R. Sottong, Arnold, MD (US); Richard J. Kowalski, Rosedale, MD (US)

(73) Assignee: Cylex, Inc., Columbia, MD (US)

( * ) Notice: Subject to any disclaimer, the term of this patent is extended or adjusted under 35 U.S.C. 154(b) by 420 days.

(21) Appl. No.: 10/411,353

(22) Filed: Apr. 11, 2003

(65) Prior Publication Data

US 2003/0199006 A1   Oct. 23, 2003

Related U.S. Application Data

(60) Provisional application No. 60/371,402, filed on Apr. 11, 2002.

(51) Int. Cl.
*C12Q 1/66* (2006.01)
*G01N 33/54* (2006.01)

(52) U.S. Cl. .................. 435/7.24; 435/8; 436/827
(58) Field of Classification Search .............. 435/5, 435/7.22, 7.24, 7.32, 8, 30; 436/827
See application file for complete search history.

(56) References Cited

U.S. PATENT DOCUMENTS

| | | | |
|---|---|---|---|
| 4,677,061 A * | 6/1987 | Rose et al. ................ 435/7.24 |
| 4,778,750 A | 10/1988 | Gottlieb ........................ 435/5 |
| 4,959,302 A * | 9/1990 | Cornaby et al. ................ 435/5 |
| 5,292,636 A * | 3/1994 | Kung et al. ..................... 435/5 |
| 5,445,939 A | 8/1995 | Anderson ................... 435/7.24 |
| 5,569,585 A * | 10/1996 | Goodwin et al. ............... 435/6 |
| 5,773,232 A | 6/1998 | Wier ........................ 435/7.24 |
| 6,150,121 A * | 11/2000 | Hamawy et al. ........... 435/7.24 |
| 6,251,616 B1 * | 6/2001 | Barbera-Guillem et al. ...... 435/7.24 |
| 2002/0150952 A1 * | 10/2002 | Sottong et al. ............. 435/7.21 |
| 2003/0199006 A1 * | 10/2003 | Britz et al. ................. 435/7.21 |

OTHER PUBLICATIONS

Article titled: "Immune cell function testing: an adjunct to therapeutic drug monitoring in transplant patient management" Kowalski; Post; Schneider; Britz; Deierhol; Lobashevsky; Redfield; Schweitzer; Reardon; Davis; Bentlejewski; Heredia; Fung; Shapiro; Zeevi; Thomas. From the Clinical Transplantation magazine pp. 77-88 dated 2003.

* cited by examiner

*Primary Examiner*—David A. Saunders
(74) *Attorney, Agent, or Firm*—Whitham Curtis Christofferson & Cook, PC

(57) ABSTRACT

Methods for monitoring the immune response and predicting clinical outcomes for patients on immunosuppressive drugs (such as transplant patients) are provided. The methods are based on the measurement of an intracellular metabolic marker in lymphocytes (such as ATP) as an indicator of a patient's immune response.

9 Claims, 8 Drawing Sheets

_US 7,476,514 B2_

METHOD FOR MONITORING THE IMMUNE RESPONSE AND PREDICTING CLINICAL OUTCOMES IN TRANSPLANT RECIPIENTS

This application claims priority to U.S. Provisional Application 60/371,402 filed Apr. 11, 2002, the complete contents of which is hereby incorporated by reference.

BACKGROUND OF THE INVENTION

1. Field of the Invention

The invention generally relates to methods for monitoring the immune response in a patient receiving immunosuppressive drugs. In particular, the invention provides methods based on the measurement of metabolic markers of activation in immune cells as an indicator of the patient's immune response. The methods may be used to predict clinical outcomes and determine treatment courses for patients such as transplant recipients.

2. Background of the Invention

Each year, 55,000 organ transplants are performed worldwide.[1] Cumulatively, the number of living organ recipients is now estimated to be over 300,000. Most of these transplant recipients will remain on immunosuppressive drugs for the remainder of their lives to prevent rejection episodes. Controlled doses of these drugs are required to prevent overmedication, which may leave the patient susceptible to opportunistic infection, increased risk of cancer and cardio-vascular disease, and drug toxicity effects, or under-dosing, which may lead to shortened graft survival due to rejection episodes.

The two major drugs used in transplant maintenance today are cyclosporin (Novartis) and Tacrolimus[1] (Fujisawa). These drugs are inhibitors of calcineurin, a key enzyme involved in T cell activation.[2] Therapeutic drug monitoring (TDM) for these two immunosuppressive drugs is routinely performed, as prescribed by the manufacturers. However, the amount of drug measured in the blood does not directly correlate with the dose of drug administered because of individual pharmacokinetic differences.[3] In addition, the level of drug determined by immunoassay is not correlated with immunosuppressive drug efficacy.[4] Therefore, the main value of these TDM tests is the avoidance of toxic levels and monitoring patient compliance.

There is currently no method available for the direct assessment of immune status in transplant recipients.

SUMMARY OF THE INVENTION

The subject invention provides a method of monitoring immune responses in a patient who is being evaluated as an organ recipient and/or is receiving at least one immunosuppressive drug. This convenient and reliable method includes the steps of analyzing the immunological responses of a set or subset of lymphocytes from a blood sample by determining at least one level of functional activity and comparing it with the immunological responses of lymphocytes with defined levels of human immunological responses (low, moderate or strong). The immune status assessment of the patient is based on this comparison. Immunological responses are ascertained by measuring an intracellular component that is increased if the cells have responded to a stimulus.

In an advantageous embodiment, the patient is a transplant recipient. For example, the patient may be a recipient of a heart, lungs, kidney, pancreas, liver, small bowel or other organs, tissues, or bone marrow transplant. At least one immunosuppressive drug may be administered, for example, calcineurin inhibitors, enzyme inhibitors, antimetabolites, lymphocyte depleting drugs, corticosteroids, or other immune modulators. Drug combinations may also be administered. The overall effect of drugs on immune responses may be measured using an assay which detects increases in an intracellular component, for example ATP, by a mitogen or antigen stimulation and then employing a luciferase assay, or by measuring other metabolic intermediates such as NADP, ionic metabolites such as $Ca^{2+}$, or proteins involved in cell cycle regulation such as PCNA.

One aspect of the invention is a method for predicting a clinical outcome in a patient who is receiving none or one or more immunosuppressive drugs. The method utilizes measured ranges of lymphocyte responses derived from a cohort of apparently healthy individuals as a means of defining normal ranges of reactivities, and includes the steps of determining at least one value of lymphocyte response in a sample of blood from a patient before or after administration of immunosuppressive drug(s); determining whether the lymphocyte response of the cells from the patient receiving the immunosuppressant drug is higher or lower than the range defined for apparently healthy individuals, or falls within it; and providing a guide for therapy and predicting a clinical outcome based on the comparison. Clinical outcomes or conditions which may be predicted include transplant rejection, overmedication, and infection. For example, a lymphocyte response that falls in the low range indicates high immunosuppression and may be indicative of over-medication which may lead to organ toxicity, infection, or, in the long term, cancer. A lymphocyte response which falls in the strong range indicates a low immunosuppressed condition, which may be indicative of infection or a course leading to organ rejection. Alternatively, a lymphocyte response which falls in the moderate range may indicate that stability of the immunological response has been achieved and that no changes in therapeutic regimen are warranted at that time.

Another aspect of the invention is to use the assay to monitor patients who are being weaned from the immunosuppressant drug(s), or for measuring patient compliance with medication prescriptive instructions.

In yet another aspect, the invention provides a method for assessing the pharmacodynamic impact (physiological effect) of an immunosuppressant drug in a non-transplant patient. The method includes the steps of determining a value of an immune response in at least one sample of lymphocytes from the non-transplant patient; comparing the value with values in a reference set comprising ranges of values of immunological response for lymphocytes; and assessing the pharmacodynamic impact of the immunosuppressant drug based on a comparison made in said comparing step. The non-transplant patient may be receiving the immunosuppressant drug for a disease condition such as autoimmunity, inflammation, Crohn's Disease, lupus erythromatosus, or rheumatoid arthritis. The method will typically be carried out in order to reduce complications from infections or cancer in the non-transplant patient.

DETAILED DESCRIPTION OF THE PREFERRED EMBODIMENTS OF THE INVENTION

Figure 1:
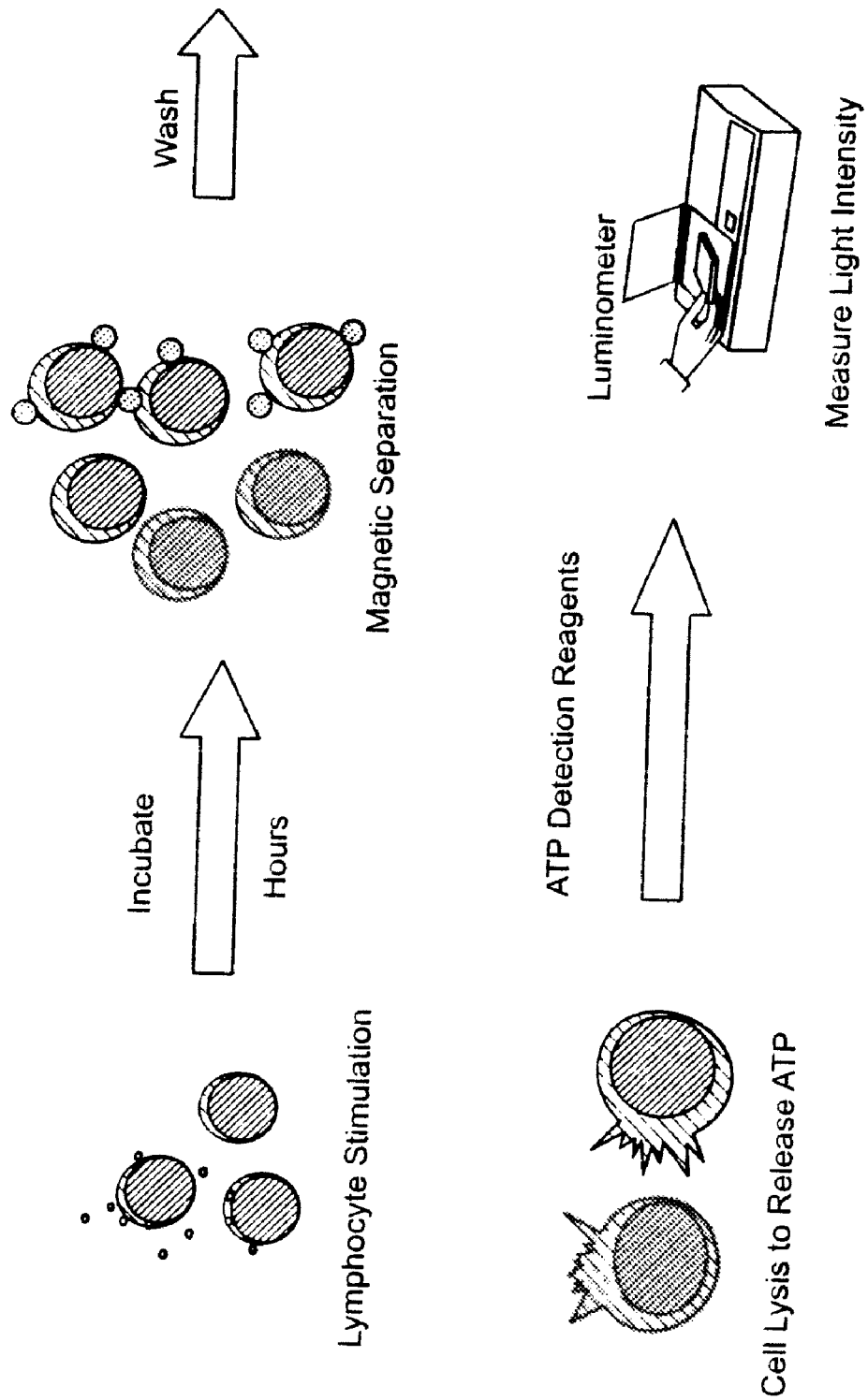
FIG. 1: Schematically illustrates an immune cell function assay as set forth in U.S. Pat. No. 5,773,232 which is herein incorporated by reference in entirety. Lymphocytes are stimulated, incubated, and CD4+ cells are separated via magnetic separation; cells are washed and lysed to released ATP, which is detected.

The present invention provides methods of determining and/or monitoring the state of an individual's immune system. The methods involve measuring the level of metabolic markers of cellular activation in a subset of immune cells as a measure of immune response, and assignment of the immune response to a standardized range or zone of immune reactivity. The practice of the method thus provides a single time point "snapshot" of the individual's immune response. Alternatively, by monitoring an individual's immune response at several time points, it is possible to obtain a complete picture of the immune system's reactivity over time. The methods of the present invention make it possible to observe, for example, the response of a patient's immune system to a medical procedure and to adjust treatment protocols accordingly. In addition, the inventors have discovered that, using the methods of the present invention, it is possible to predict certain clinical outcomes related to immune system functioning. For example, in a preferred embodiment of the invention, a patient whose immune system is monitored may be on an immunosuppressive drug therapy regimen. In some embodiments, the immunosuppressive drug(s) are administered as the result of an organ transplant. By monitoring the immune response of such a patient, it is possible to predict a risk of rejection of the transplanted organ; or to ascertain if the patient is overmedicated, a condition which can contribute to an increased risk of opportunistic infection, organ toxicity or cardiovascular complication.

Examples of metabolic markers of cellular activation that can be measured in the practice of the present invention include but are not limited to adenosine triphosphate (ATP), nicotinamide adenine dinucleotide phosphate (NADP), proliferating cell nuclear antigen (PCNA), and/or $Ca^{2+}$ ions. Examples of subsets of immune cells in which a metabolic marker can be measured include but are not limited to subsets of lymphocytes such as CD4, CD3, CD19 and CD56 cells.

In one embodiment of the present invention, the state of the immune system is ascertained by measuring the level of ATP present in CD4 cells. In order to make an ATP measurement, a sample of whole blood is obtained from the patient. Certain advantages accrue from using whole blood in the incubation. For example, the immunosuppressive drugs and antigen presenting cells required for cellular activation are retained in the sample, the cells are maintained in their own plasma, and an initial prepurification step is eliminated. The whole blood sample is incubated with at least one stimulant. Examples of suitable stimulants include but are not limited to mitogens (for example, the plant mitogens phytohemagglutinin, Concanavalin A or Pokeweed mitogen); alloantigens (which may be, for example, located on a cellsurface, selectively purified, or bound to a synthetic surface e.g. plastic); autoantigens (which also may be, for example, located on a cell surface, selectively purified, or bound to a synthetic surface e.g. plastic), and foreign antigens such as those which originate from bacteria, viruses, and various parasitic organisms. Examples of viruses include but are not limited to polyoma viruses (e.g. human polyoma virus BK, polyoma virus JC), human papilloma virus or cytomegalovirus (CMV). In preferred embodiments of the invention, the stimulant is a mitogen such as the plant mitogen phytohemagglutin. After sufficient incubation time, the CD4 cells are removed from (i.e. isolated from) the sample. In general, the time for incubation of the whole blood sample and the mitogen is in the range of hours to days, and preferably in the range of about 0.5-6 to about 24-48 hours. The CD4 cells are then removed, e.g. by using paramagnetic particles containing an antibody specific for CD4 cells. However, those of skill in the art will recognize that removal of the CD4 cells may be carried out by any of a variety of means which are well known, such as column separations, panning, or by using plastic or ferrous particles with ligands for the immune cell attachment.

The isolated CD4 cells are then lysed, and the level of ATP in the lysate is quantified. Methods of lysis are well known in the art. Detection of ATP can be accomplished by any of several suitable methods, such as enzyme analysis, high pressure liquid chromatography (HPLC), or thin layer chromatography (TLC). However, in a preferred embodiment, the ATP is detected by a luciferin-luciferase assay. An alternative is that the cells are not lysed, and the activation product is measured inside the cell via cytometry, colorimetrically or by chemiluminescent reporter.

The inventor's have discovered that the immune response of an individual at any point in time may be classified according to the amount of a metabolic marker of activation in immune cells that is detected. For example, a level of ATP that is detected in a patient may be quantified versus known standard levels of ATP detected in apparently healthy individuals and generated using a calibration curve. The invention thus also provides a system for classifying an immune response as low, moderate, or strong; or alternatively, for assigning an immune response to a low, moderate, or strong range or zone of reactivity. In one embodiment of the classification system of the present invention, ATP is the metabolic marker, and an immune response is low if the level of ATP detected is 225 ng/mL or less, moderate if the level is greater than 225 ng ATP/mL but less than 525 ng ATP/mL, and strong if the level is 525 ng ATP/mL or greater. Thus, an individual's immune response may be ranked as low, moderate or strong based on the level of metabolic marker (e.g. ATP) that is detected.

In addition to obtaining a measurement of an individual's immune system response at a single time point, it may frequently be useful to compare metabolic marker levels obtained at several time points, for example, in order to monitor the impact of a course of events on an individual's immune system. For example, ATP levels may be monitored before, during and after drug therapy, or before and after organ transplant surgery is performed, in order to monitor changes over time in the immune response of the patient in response to these medical procedures. This information regarding the patient's immune status may be useful as an adjunct to therapeutic drug monitoring at any point in the course of therapy in order to assess the progress of a patient, the suitability of a drug regimen, and to predict clinical outcomes for a patient (see below).

The present invention provides methods of determining and monitoring the state of a patient's immune system in response to a stimulus. In some embodiments, the patient is one who is receiving or will be receiving an immunomodulating drug or drugs. For example, the patient may be the recipient of an organ such as heart, lungs, kidney, pancreas, liver, bowel, skin, bone marrow or other organs. Further, a transplant patient may be the recipient of more than one organ, e.g. a "heart-lung" transplant recipient. Alternatively, the transplant may be transplanted tissue. The transplanted tissue or organ(s) may be from any source known to those of skill in the art, for example, from a live organ donor such as a relative (e.g. a sibling) or a matched non-related donor; from a cadaver; or from a tissue or artificial "organ" that has been developed and/or maintained in a laboratory setting, e.g. tissue or "organs" grown from stem cells, or cultured in a laboratory setting from tissue or cell samples. Alternatively, the patient may be under treatment for an autoimmune disease such as rheumatoid arthritis, lupus, Crohn's disease, psoriasis, etc. Or the patient may be afflicted with an infectious disease, such as Human Immune Deficiency Syndrome related viruses (HIV-1), or Hepatitis associated viruses (HCV). Further, the patient may be a cancer patient. Those of skill in the art will recognize that the methods of the present invention may be used to monitor and/or assess the immune system of any individual for any reason.

In yet another aspect, the invention provides a method for assessing the pharmacodynamic impact of an immunosupressant drug in a non-transplant patient. The method includes the steps of determining a value of an immune response in at least one sample of lymphocytes from the non-transplant patient; comparing the value with values in a reference set comprising ranges of values of immunological response for lymphocytes; and assessing the pharmacodynamic impact of the immunosupressant drug based on a comparison made in said comparing step. The non-transplant patient may be receiving the immunosupressant drug for a disease condition such as autoimmunity, inflammation, Crohn's Disease, lupus erythromatosus, or rheumatoid arthritis. The method will typically be carried out in order to reduce complications from infections or cancer in the non-transplant patient.

Those of skill in the art will recognize that many types of immunosuppressive drugs exist that may be administered, the effects of which on the immune system of a patient may be monitored by the methods of the present invention. Examples include but are not limited to antilymphocyte drugs such as OKT3, Antithymocytegamma globulin (ATGAM), Daclizumab, and Basiliximab (anti IL2R); calcineurin inhibitors such as Tacrolimus (Prograf®, FK506) or cyclosporin (Neoral®); antimetabolites such as Azathioprine, Cyclophosphamide, and Mycophenolate mofetil; enzyme inhibitors such as Sirolimus (Rapamune), or corticocorticoids such as Prednisone, or methylprednisolone (Solumedrol.).

The present invention provides a method of guiding decisions regarding therapies and of predicting a clinical outcome of a patient receiving one or more immunosuppressive drugs. Possible clinical outcomes include, for example, rejection of the transplanted organ, infection, or organ toxicity. In order to predict clinical outcomes such as these, it is advantageous to determine an initial level of the immune response as early in the immunosuppressive drug course as possible in order to start surveillance of the patient's immune status coincident with or soon after transplant surgery, but monitoring may begin at any point after the administration of the immunomodulating drugs. Subsequent immune responses are ascertained and compared to the earlier response, and to each other. Any given immune response value (ATP ng/mL) can be assigned to a category of a known range of values, and a comparison of changes in measured values over time allows the observation of trends in the immune response of the patient. For example, the patient's immune response at any point in time may be classified as low (ATP ng/mL $\leq$225), moderate (ATP ng/mL >225 and <525), or strong (ATP ng/mL $\geq$525), and a trend toward a heightened or diminished immune response can be observed.

In a preferred embodiment, an initial blood sample is obtained and tested prior to organ transplant surgery and before any immunosuppressant drug is administered. The immune response value is ascertained and compared to the categories of known value ranges (e.g., low, moderate or strong). Based on these values the initial drug dose may be maintained within or modified from the usual practice of dose assignment on the basis of patient body weight. For example, a transplant candidate who is determined to be immunosuppressed due to an infectious disease (e.g. AIDS) may be given a lower or no drug dose, compared to another individual of the same body weight.

In another preferred embodiment, an initial blood sample is obtained and tested prior to organ transplant surgery and before any immunosuppressant drug is administered, and another blood sample is tested after surgery and after the administration of drugs. By comparing the values obtained from these samples, medical judgements can be made relative to the effect of the surgery and drugs on the patient specifically regarding the immune status. For example, if the value obtained from the sample obtained subsequent to the first was in a lower range than the first, additional testing may be indicated and or medication doses reduced to avoid the possibility of over medication. If the value obtained from the sample obtained subsequent to the first one was in a higher range than the first, additional testing may be indicated and or medication doses increased to avoid the possibility of organ rejection.

In another preferred embodiment, a blood sample obtained and tested at any point after surgery can provide immune status information regarding the level of immune suppression when the values are compared to categories of known value ranges. For example, if the value obtained is in the weak range, additional testing may be indicated and or medication doses reduced to avoid the possibility of over medication. If the value obtained is in the strong range, additional testing may be indicated and/or medication doses increased, or rescue therapy initiated to avoid the possibility of organ rejection. Further, if the value is in the moderate range, and particularly if the value does not fluctuate significantly (e.g. stays within the same zone) for at least two consecutive monthly measurements, this may indicate that stability of the immune response has been achieved, and that adjustments to the treatment regimen are not necessary at that time.

Regarding the frequency at which blood samples are analyzed, those of skill in the art will recognize that sampling may be done at any point at which a skilled practitioner (e.g. a physician) deems it to be advisable. In general, such testing would be carried out at most daily (e.g. during a time when a patient is most at risk) and at least monthly (e.g. during a time when a patient appears to be relatively stable).

In yet another preferred embodiment, multiple blood samples are obtained and tested at multiple points after the organ transplant surgery and during the period when immunomodulating drugs are being administered. An example of the predictive value of the methods would be the detection, by utilizing the methods of the present invention, of an increase in the immune response of the patient from the low to moderate to the strong range over a period of time. The results may be predictive of potential acute rejection of the transplanted organ, and may warrant, for example: initiation of other confirmatory tests (e.g. organ biopsy or organ specific blood chemistry analyses); an increase in the dose of the drug being administered; a rescue therapy with an alternate drug; or a new combination of drugs. In general, in order to predict potential organ rejection, the state of the immune response must be monitored for several days, and preferably for about 3-5 days. In the case of monitoring ATP, in order to conclude that a risk of organ rejection exists, the immune response of the patient must show an increase in the range of at least about 50 ng/mL ATP to 100 ng/mL ATP.

On the other hand, an unexpected decrease in the immune response over a period of time may be predictive of the risk of developing an opportunistic infection due to over medication. For example, if a patient's immune response declines from the moderate range to the low range, this may be indicative of over-medication and warrant the initiation of further confirmatory tests (e.g. organ biopsy or organ function analysis, or assays for infectious organisms by PCR), or a reduction or change in medication. In general, in order to detect possible over medication, the state of the immune response must be monitored for several days, and preferably for about 3-5 days. In order to conclude that a risk of overmedication exists, the immune response of the patient must show a decrease in the range of at least about 50 ng/mL to 100 ng/mL ATP.

The method may further be useful for monitoring a patient's immune response during the standard immunosupressive-therapy phase of "weaning" the patient from the drugs, i.e. the phase during which a patient's drug dosage is lowered as much as possible to reduce the risk of toxicity, while maintaining a low chance of transplant rejection. In particular this assay is especially valuable for monitoring tolerance protocols where the objective is the eventual removal of all immunosuppressive drugs. For example, drugs doses may be reduced in a patient whose FK506 (Tacrolimus) blood drug level is greater than 15 mg/mL, to 6-10 mg of FK506 per Kg of body weight 2-3 times per week until the desired immune response level is attained. Similarly, the method may also be used to assess patient compliance with prescribed medication regimens.

The method is also of value in monitoring the functional status of the immune responses of long-term organ recipients, who have been on the same medication dosages for extended time periods (years). Patients who have taken immunosuppressive drugs over a long period have been shown to suffer from over suppression concurrent with extended drug courses.

The methods of the present invention may be used alone as the primary means of tracking a patient's progress. More frequently, the methods will be used in conjunction with and as an adjunct to other means of assessing a patient's progress, for example, monitoring drug levels in the blood, organ biopsy, organ specific blood chemistry tests, and the like.

EXAMPLES

Materials and Methods

Study Design.

A multicenter study was conducted with a cohort of 155 apparently healthy adults and 127 organ transplant recipients. The inclusion criteria for healthy adults, living donor candidates, and volunteers consisted of men and women between the ages of 19 and 64 who were eligible to donate blood according to established blood donation guidelines. The inclusion criteria for transplant recipients consisted of men and women aged 19 to 64 who were recipients of cadaveric, living-related, or living unrelated kidney, liver, or pancreas organs. Transplant patients were excluded from the trial if they were infected with human immunodeficiency virus or if they were more than five (5) years post transplant.

The apparently healthy adult population who were blood donors consisted of 24% (37) females, 68% (105) males and 8% (13) undesignated, with an age range of 20-60 years. The ethnicity of the population was 59% (91) African American, 28% (44) Caucasian, and 13% (20) other. The transplant population consisted of 43% (55) females, and 57% (72) males, with an age range of 20 -64 years. The ethnicity of the population was 24% (31) African American, 69% (87) Caucasian, 7% (9) other. The organs transplanted were, 59% (75) kidney, 34% (43) liver, 2% (3) pancreas and 5% (6) multiple organs (simultaneous kidney and pancreas).

Patient History.

Transplant patient history included the condition predisposing patient for transplant, organ(s) transplanted and their source (cadaver or living related or unrelated), type of immunosuppressive therapy, time relative to transplant, dosage and blood levels of immunosuppressive drugs at time of sample collection, gender and age.

Therapy Protocols.

The types of immunosuppressive therapies were not limited during this study. The standard of care protocol at each center for transplant patients at hospital discharge and during maintenance outpatient visits was followed. The types of therapy included: induction therapy with OKT3 or ATG; calcineurin inhibitors including Tacrolimus (Prograf®) or cyclosporine-A (Neoral®); steroids (prednisolone); and mycophenolate mofetil (MMF) Celicept®. Use and dosage were based on standard practice at each center and varied both within and between centers.

Sample Collection.

Two whole blood samples (one each, sodium heparin and EDTA anticoagulated Vacutainer® tubes) (B-D, Franklin Lakes, N.J.) were drawn from apparently healthy adults and transplant patients. Samples collected in sodium heparin vacutainer tubes (green-tops) were used for the Cylex™ Immune Cell Function Assay ImmuKnow™ and samples collected in EDTA vacutainer tubes (lavender-tops) were used for flow cytometry. Samples were handled and tested according to each manufacturer's package insert.

Cylex™ Immune Cell Function Assay[5] (ImmuKnow™)

Whole blood (100 μl of a 1:4 dilution) was tested in quadruplicate with or without phytohemagglutinin (PHA) (2.5 μg/mL) overnight (15-18 hours in a $CO_2$ incubator at 37° C.). Anti-human CD4 monoclonal antibody coated magnetic particles (Dynal Biotech A.S.A., Oslo, Norway) were added to immunoselect CD4 cells from both the stimulated and non-stimulated wells. After washing the CD4 cells selected on a strong magnet (Cylex™ Cat. 1050) a lysing reagent was added to release intracellular ATP. A luciferin/luciferase mixture was then added to the cell lysate. Within 30 minutes after addition of enzyme, the bioluminescent product was measured in a luminometer (PHL Mediators, Austria or Berthold, Maryville, Tenn., or Turner Designs, Sunnyvale, Calif.) (See FIG. 1). The amount of light emitted (emission maximum 562 nm) was compared to a standard curve generated with ATP calibrators (0, 1, 10, 100, 1000 ng/mL). The concentration of ATP (ng/mL) in each sample was then calculated from the calibration curve using an Excel-based program provided by Cylex™.

Therapeutic Drug Monitoring

The trough levels of cyclosporin or Tacrolimus were performed on whole blood using a microparticle enzyme immunoassay (MEIA) on the IMx immunoassay system according to the manufacturer's instructions (Abbott Diagnostics, North Chicago, Ill.).

Statistical Analysis

The Cylex™ Immune Cell Function Assay ImmuKnow™ results from apparently healthy adults and transplant patients were analyzed by ANOVA or two-tailed t Tests[6] to assess the statistical significance of differences. A double probability plot (modified ROC Analysis) was used to establish three zones of immune reactivity in the two populations[7].

Example 1

Cylex™ Immune Cell Function Assay (ImmuKnow™): Principle of the Assay

Successful management of the transplant recipient currently requires lifelong immunosuppression of the patient to avoid graft rejection[13]. While calcineurin inhibitors have dramatically improved graft survival, the patient is at increased risk of drug toxicity, opportunistic infections and cancer[14]. Managing the relatively narrow therapeutic range of these drugs remains one of the challenges of transplant medicine. While tests for the trough levels of the major transplant drugs are routinely performed for patient monitoring, their main value is the avoidance of toxicity and assessing patient compliance[15]. Prior to the present invention, no test existed which directly measured the bioactivity of these drugs in the patient at any point in time. The methods of the present invention were designed specifically to assess the immune response in patients receiving immunosuppressive drugs.

The immunosuppressive therapy requirements for patients undergoing transplant are a function of a large number of variables, including the underlying disease which led to the transplant, degree of histocompatibility matching and pretransplant sensitization, organ type, as well as the individual patients ability to metabolize the drug. Once the transplant is performed and therapy initiated, the trauma of surgery, anesthesia, and possibly blood transfusions will collectively impact the patient's net state of immunosuppression.[16] No tests performed today allow the assessment of the patient's immune status either prior to surgery or during the post-transplant period, now averaging 10 years. This application describes the results of a multicenter trial which was designed to statistically establish ranges of immune reactivity in recipients of solid organ transplants using an assay for the measurement of T-cell mediated immunity using the Cylex™ Immune Cell Function Assay (ImmuKnow™), which is depicted in FIG. 1.

The Cylex™ assay uses a whole blood sample which is stimulated with the plant mitogen, phytohemagglutinin (PHA). Whole blood was deliberately chosen as the sample to maintain the lymphocytes in the presence of the immunosuppressive drugs, which are partitioned between the red cells and the plasma [17]. In addition, while the prepurification step is avoided, the cells are also maintained in their own plasma, avoiding the additional stimulation from foreign serum which would be required to incubate purified cells. Phytohemagglutinin was the stimulus of choice because transplant patients may be anergic and not expected to respond to weaker stimuli including recall antigens or alloantigens. In addition, since cyclosporine and Tacrolimus were designed to inhibit total T cell activity, a broad spectrum mitogen (like PHA) is most appropriate. Among mitogens, PHA is more potent than Concanavalin A, or pokeweed mitogen. Therefore, in highly suppressed patients, some "breakthrough" response might still be expected.

Traditionally, lymphoproliferation (LPA) has been used as an in vitro model for cell-mediated immunity[18]. In healthy adults undergoing vaccination with tetanus, the Cylex™ assay gave comparable results to lymphoproliferation[10]. Dose response curves of the PHA response, comparing a whole blood adaptation of LPA, showed greater sensitivity of the Cylex™ assay to lower doses of PHA with responses measurable at 24 hours vs. 3 days for LPA[10].

LPA has several disadvantages because it requires 3 to 7 days to perform and uses radioactive tritiated thymidine[18]. Perhaps more importantly, peripheral blood monocytes are purified from the blood prior to culture, thereby removing the red cells in which the major calcineurin inhibitors are sequestered. Zeevi[17] recently demonstrated that recall responses, alloreactivity, and PHA-induced activation were also suppressed in the whole blood ATP assay while proliferation in isolated PBMC were still measurable in transplant recipients receiving immunosuppressive therapy. One possible explanation is that removal of red cells and the prolonged incubation time (3-7 days) of LPA allowed the recovery of cells from immunosuppression which cannot occur in the human physiological model. Others have since demonstrated that red blood cells from transplant patients added back to LPA cultures can restore immunosuppressive activity in vitro.

Following overnight incubation of blood with PHA, CD4 cells are selected using paramagnetic particles (Dynal) coated with a monoclonal antibody to the CD4 epitope. CD4 positive cells which orchestrate both cellular and humoral immune responses are targeted since the major immunosuppressive drugs were designed to specifically inhibit T cell activation which has been implicated in rejection[19]. Both cyclosporin and Tacrolimus inhibit T cell activation by reducing transcription of IL-2[26].

Most immune cell functions depend directly or indirectly on the production of ATP[8]. Weir (U.S. Pat. No. 5,773,232 the complete contents of which is hereby incorporated by reference) originally patented the use of ATP as a marker of lymphocyte activation[5]. When assessing the immune status of transplant patients on cyclosporin or Tacrolimus, cellular ATP is an appropriate target because both compounds inhibit mitochondrial respiration, which is a major source of intracellular ATP[20,21].

Therefore, reduced ATP production directly inhibits the cascade of steps required for lymphocyte functionality including transcription of cytokine mRNA, cytokine production, and ultimately lymphocyte proliferation, which is also largely cytokine dependent. In a direct comparison of the kinetics of ATP production and cytokines, ATP preceded the appearance of most cytokines measured[26].

Transplant recipients receiving immunosuppressive therapy are generally weakly or non-responsive to skin tests and show inhibited cytokine responses in vitro[4] (Ahmed et al.). The Cylex™ Immune Cell Function Assay (ImmuKnow™) uses the plant lectin phytohemagglutinin (PHA) to stimulate activation of lymphocytes[5]. Since most of the effector functions of immune cells depend upon cellular energy supply[8], the assay was designed to measure increases in intracellular ATP following activation by mitogenic, recall antigen, or allogeneic stimulation[9,10,11]. Given that the target of the major immunosuppressive drugs, cyclosporin and Tacrolimus, is T cell function, CD4 cells were selected for measurement. Both cyclosporin and Tacrolimus are lipophilic drugs which partition in the red cell membranes. The assay uses a whole blood sample to maintain the presence of the drug during the incubation. Use of whole blood not only avoids the necessity of pre-purification of lymphocytes but also maintains an environment for effective antigen presentation. By using whole blood, the patient's own plasma is present during the overnight incubation, rather than foreign serum (human AB or fetal calf), which might provide exogenous stimulation[11]. Patient samples may be used up to 30 hours after collection. Since incubations are overnight, testing can be batched at the end of each day.

A schematic representation of the assay is given in FIG. 1. The assay was used to obtain the results presented in the Examples 2-12.

Example 2

Figure 2:
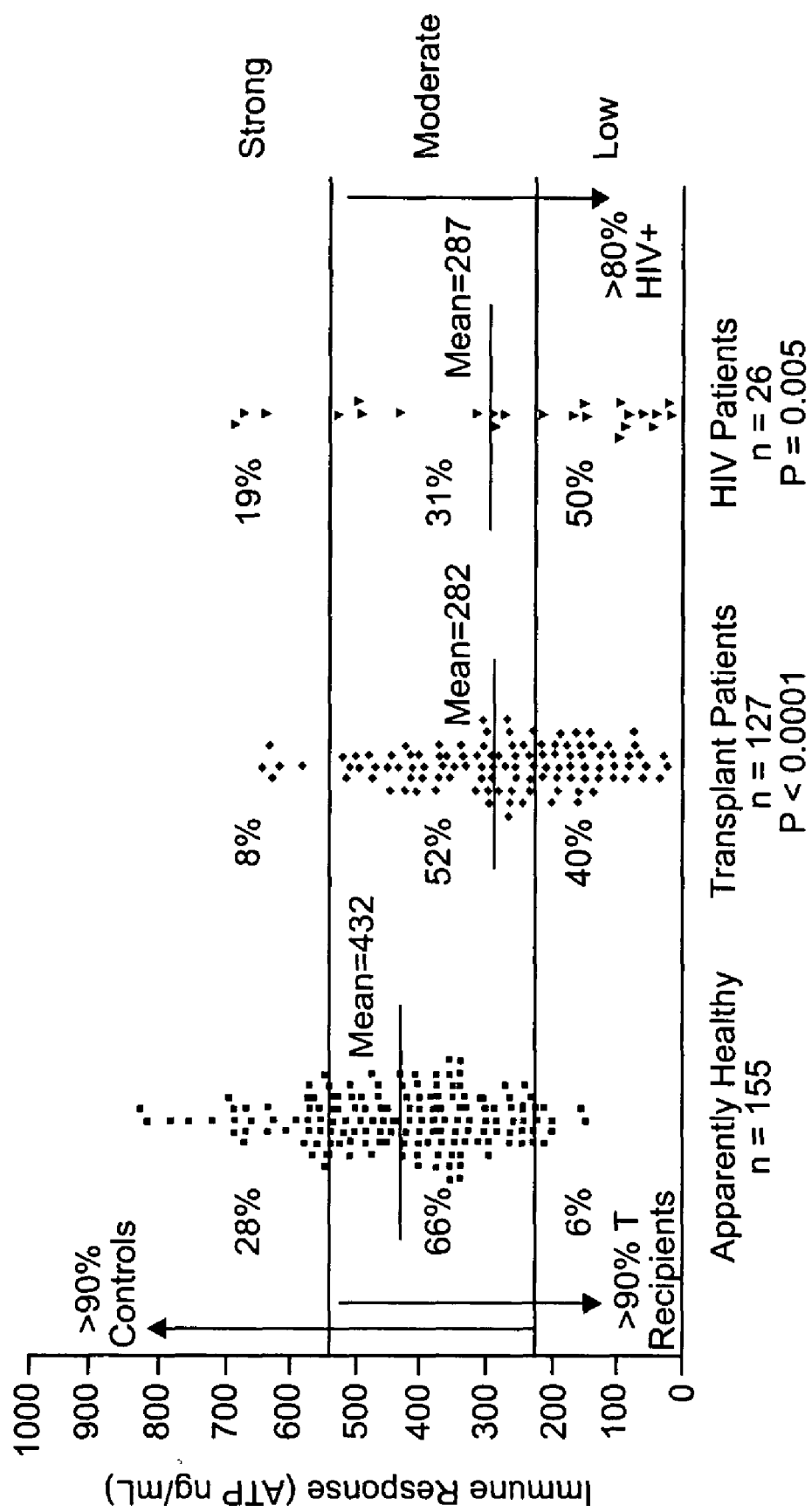
FIG. 2: Immune response distributions of apparently healthy adults, transplant recipients and HIV patients. Y axis=ATP (ng/mL). Zones of low ($\leq 225$ ng/mL ATP), moderate (>225 ng/mL ATP and <525 ng/mL ATP) and strong (≧525 ng/mL ATP) immune response are indicated.

Statistical Characterization of the Immune Response Levels of Healthy Adults and Immunosuppressed Populations A population-based study was conducted comparing the immune response characteristics of apparently healthy adult controls and recipients of solid organ transplants. As shown in FIG. 2, the apparently healthy control population (n=155) gave a stimulation response on average of 432 ng/mL ATP. The immune response characteristics of transplant recipients (n=127) were significantly statistically lower (P<0.0001) than healthy controls by over 150 ng of ATP, and averaged 282 ng/ml ATP. Statistical comparison of the two populations using a modified double probability plot allowed the description of three zones of reactivity. Ninety-two percent (92%) of the transplant patients gave immune response ATP values of less than 525 ng/mL. Ninety-four percent (94%) of apparently healthy patients gave immune response ATP values of greater than 225 ng/mL. This allows the characterization of a patient's immune response at any point in time as low ($\leqq$225), moderate (>225 but <525), or strong ($\geqq$525). Also shown is the distribution of viral-induced immunosuppressed HIV patients. This immunosuppressed population was statistically similar to transplant recipients with an average immune response of 287 ng/mL ATP.

Most immunosuppressive drugs are currently administered on the basis of body weight[13]. Yet it is clear that the baseline levels of immune response in patients awaiting transplant vary enormously. Today, no method is available for assessing the patient's basal immune reactivity or their initial response to therapy. In an effort to better predict therapeutic efficacy, Kahan[22] have proposed that patients undergo a trial dosing regimen prior to surgery. While this may not always be practical, an assay which measures a global immune response, like PHA-induced activation, can detect the net effect of surgery, anesthesia, transfusions and therapeutic drugs on immunosuppression. Therefore, following transplant, patient's responses were statistically distributed at three levels of reactivity by the Cylex™ Immune Function Assay: low, moderate or strong. These groupings provide relative measures of reactivity, especially when the patient is used as his/her own control for subsequent determinations. Following surgery and the conversion to oral therapy, the status of immune reactivity for each patient could be assessed prior to discharge. Once the patient is stabilized in the post-transplant period, the assay has utility as a measure of compliance with therapy. The Cylex™ ImmuKnow™ assay may also be used to measure the immune response during weaning patients of their immunosuppressive drugs. Reducing the drug dose results in a corresponding increase in immune response activity.

This Example demonstrates that the distribution of immune responses in healthy adults as compared to transplant recipients is statistically different. These differences can be used to categorize a transplant recipient's immune response as strong, moderate or low in order to assess the relative pharmacodynamic impact of immunosuppressant drugs in the management of the transplant patient. Similarly, this example demonstrates that the technology is further applicable to other immunosuppressed populations such as HIV infected individuals.

Example 3

Site-to-Site Comparison

Figure 3:
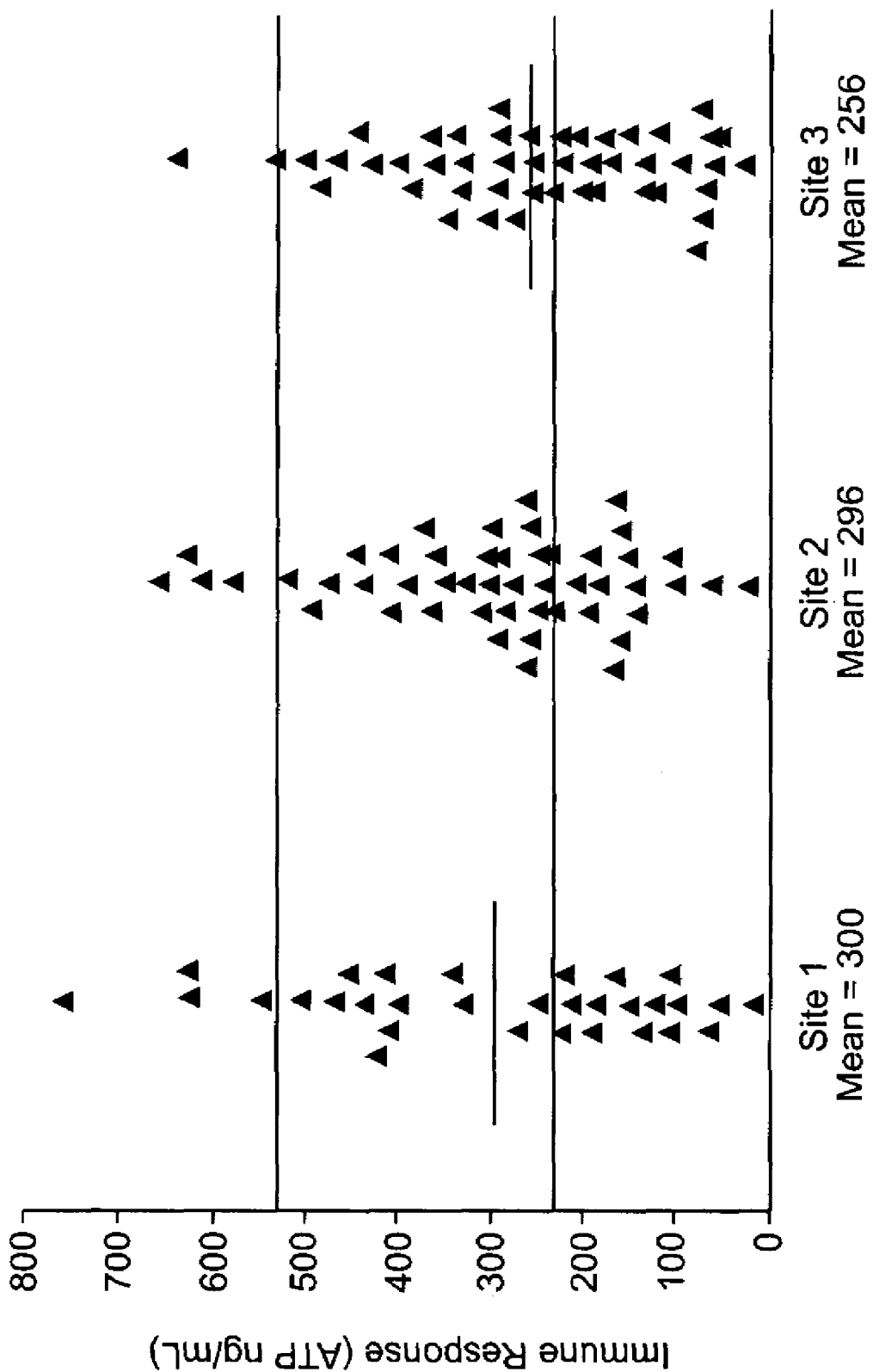
FIG. 3: Comparison of functional immune responses at three sites. Y axis=ATP (ng/mL).

A study was undertaken to ascertain the consistency results obtained using the methods of the present invention at several different clinical centers. The distributions in FIG. 3 show that there are no significant differences in patient immune responses at each of the three clinical centers. Site 1 (n=31) had a mean transplant patient immune response of 300 ng/mL ATP which was not statistically different from site 2 (n=49) or site 3 (n=47) with mean immune response values of 296 and 256 ng/mL ATP respectively.

The mean immune response at two of the three sites falls within the moderate zone. The population of patients at Site 3, which included a larger number of liver transplants, fell slightly below the moderate zone, consistent with the greater net immunosuppression in these patients resulting from the aggregate effects of more traumatic surgery and lower biological functioning.

Despite differences in populations, therapeutic protocols, and type of transplant, all three sites performed equivalently as determined by the Standard two-tailed t-Test. In addition, each laboratory was equipped with luminometers, manufactured by different vendors, and the assays were performed by technologists with a range of prior laboratory experience. All three sites demonstrated proficiency in the use of the test. Traditionally, assays for cell-mediated immunity have been difficult to standardize. For the Cylex™ Immune Cell Function Assay ImmuKnow™, an ATP calibration curve is run on each plate and reagents have been manufactured according to Good Manufacturing Practices (GMP).

These results demonstrate that the described methodology is applicable to multiple immunosupressant protocols as used by different medical institutions.

Example 4

Gender and Race Variables

The variables of gender and race were also examined. The immune responses of male and female transplant recipients as measured by ATP production were not statistically different, though males had immune responses 53 ng/mL ATP lower than females. This same trend was seen in apparently healthy adults where males gave statistically lower immune responses than females (p<0.04). In addition, the immune responses of African Americans and Caucasians could not be statistically distinguished within transplant patient populations or within apparently healthy adult populations respectively. However, on average, African Americans receive higher doses of immunosuppressive drugs at each of the clinical sites.

In the recent past, the incidence of organ transplant rejection in African Americans has been significantly higher than for Caucasians[16,23,24,25]. This difference has been attributed to increased metabolism of immunosuppressive drugs by African Americans. As a result, most protocols for African Americans now reflect the use of higher doses of immunosuppressive drugs. All three institutions in this multi-center trial adhere to such protocols. Therefore, we analyzed this population of transplant patients on the basis of ethnicity. The results demonstrated no statistical difference between African Americans, Caucasians and other ethnic groups among transplant recipients with regard to the average immunosuppression achieved. One of the questions that could be asked is whether healthy adults demonstrate different baseline responses. Apparently healthy adults also gave equivalent immune response levels in this assay. Therefore, equivalent functional suppression of all ethnic groups has been achieved across the three centers, as measured by this assay.

Statistical comparisons of immune response levels on the basis of gender was also made. Among apparently healthy adults, a marginally significant difference was seen between males and females, with males demonstrating weaker immune responses. Among the transplant recipients, although the differences were not statistically significant, males again gave lower responses to PHA in this assay when compared to females.

This Example demonstrates that despite differences in drug dosing protocols for African Americans and Caucasians, they achieve similar levels of immunosuppressive impact. By individualizing patient immunosuppressant drug management, gender and ethnic difference in immune response can be overcome by changed dosing of medication. Over-medication based on ethnicity alone can be prevented by monitoring the patient using the Cylex™ assay.

Example 5

Figure 4:
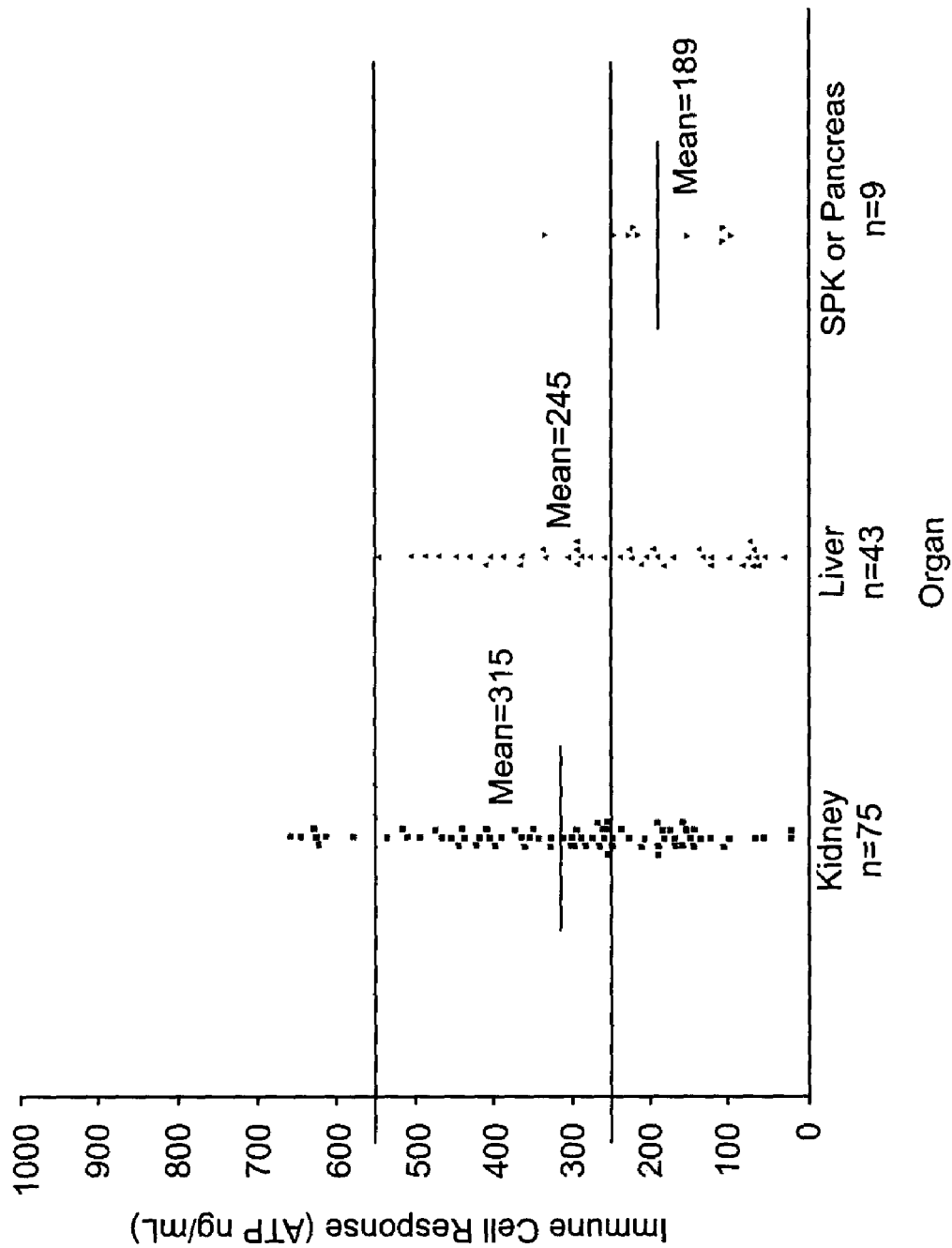
FIG. 4: Comparison of Cylex™ immune cell function response in kidney, liver and pancreas and simultaneous pancreas and kidney (SPK) recipients. Y axis=ATP (ng/mL).

Comparison of Cylex™ Immune Cell Function Response Among Types of Organ Transplanted When the average immune response is determined for patients receiving kidneys vs. livers or pancreas or simultaneous pancreas and kidney (SPK), kidney recipients exhibit stronger immune responses on average than those receiving either liver or pancreas (FIG. 4) ($p<0.05$). While most protocols prescribe higher doses of immunosuppressive drugs for kidney recipients than liver or pancreas, the liver transplant patients are generally more seriously ill. An additional explanation for the liver transplant recipients to be more suppressed is that unpaired metabolism in the liver leads to increased drug levels or prolonged half-life and therefore inhibition of immunity.

In this study, kidney transplant recipients gave statistically stronger immune responses than liver or pancreas (either alone or simultaneously with kidney). These results emphasize the importance of measuring the net immunosuppression of the patient, since it is well documented that trauma, anesthesia, transfusion and the underlying disease of the patient, as well as the therapeutic drugs all contribute to the effective level of immunosuppression. Therefore, the observation that liver patients, who receive lower doses of immunosuppressive drugs but also experience more trauma and are generally more sick than kidney patients, actually demonstrate lower levels of immune reactivity. These other factors undoubtedly contribute more in the early post-transplant period (3 months) and may account for another observation from this study that greater immunosuppression is measured in the most "stable" post-transplant period, despite the reduction in dosing of immunosuppressive drugs.

This Example demonstrates that the ability to measure net immunosuppression of an allograft recipient by taking into account the effects of medications, type of allograft, time post-transplant, trauma, and general health is valuable in managing a transplant patient appropriately.

Example 6

Figure 5:
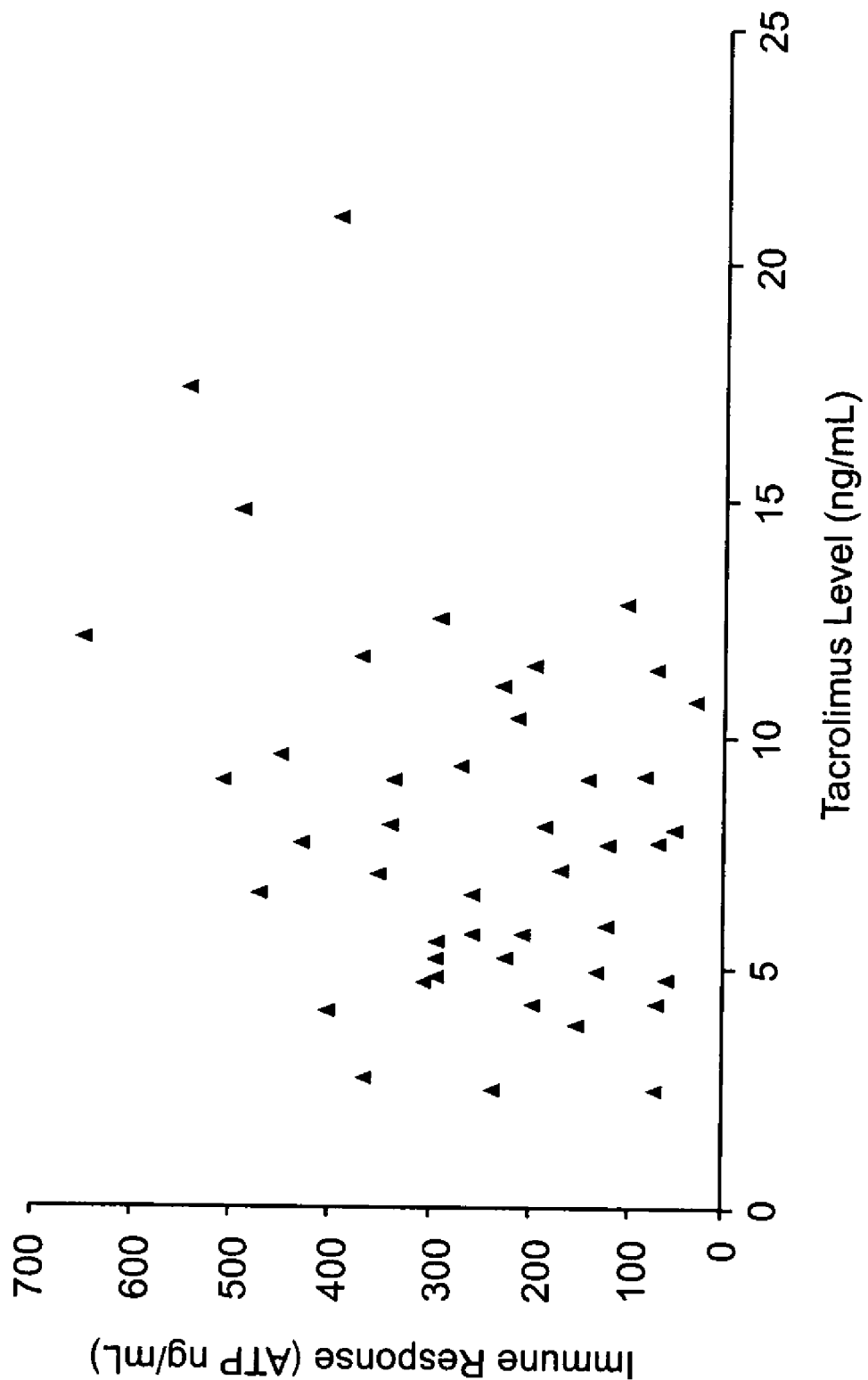
FIG. 5. Immune response versus Tacrolimus therapeutic drug monitoring trough. X axis=Tacrolimus concentration (ng/mL); Y axis=ATP (ng/mL).

Lack of Direct Correlation between Patient Immune Response Level and Therapeutic Drug Level in Blood Since the majority of patients in this study received Tacrolimus therapy, a comparison was made between the level of Tacrolimus in whole blood as detected by immunoassay, and the Cylex™ Immune Cell Function Assay (see FIG. 5). No correlation ($r^2=0.02$) was observed, emphasizing the importance of measuring a direct effect of the drug on real time immune system parameter.[4,12]

Perhaps the most important observation from this trial is that the level of Tacrolimus as measured by immunoassay of whole blood is not correlated with the degree of biological immunosuppression as measured by the PHA-induced ATP levels.

It is well known that because of pharmacokinetics differences between individuals, the does of calcineurin inhibitor administered is not correlated with the analytical level measured in the blood. These data emphasize the importance of having a functional readout of immunosuppression. Both Ahmed[4] and Shulick[12] have provided similar data using cytokine based measures of T cell function.

This Example demonstrates that the analytical measurement of immunosuppressant drug is not an adequate reflection of the pharmacodynamic impact of the drug.

Example 7

Immune Cell Response Range vs. Time Since Transplant

Figure 6:
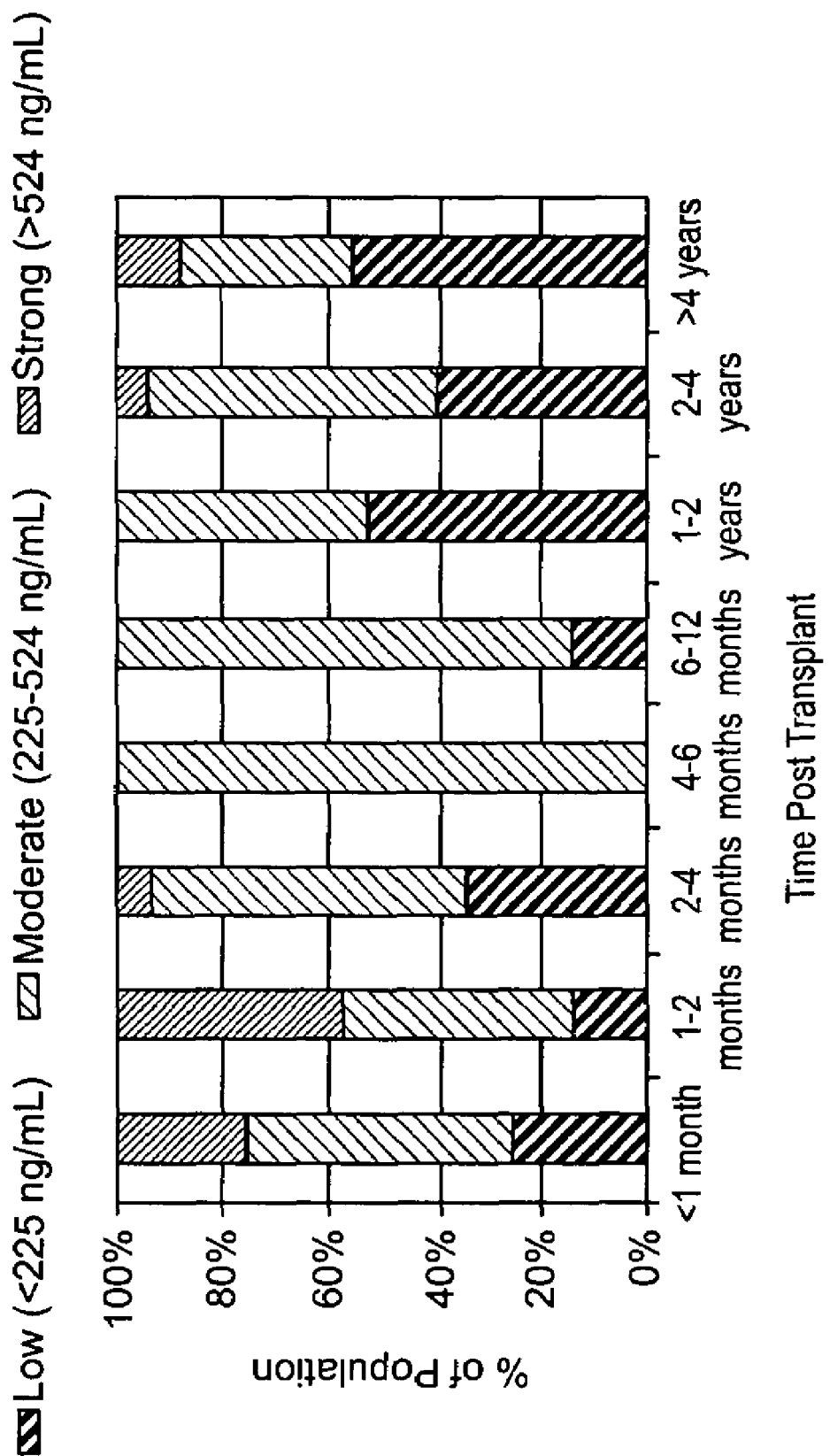
FIG. 6. Immune cell response range vs. time since transplant. Y axis tracks time since transplant; X axis is % population.

Based on the statistically established cutoffs in this study, the proportion of transplant patients who were low responders ($\leq 225$ ng/mL ATP) or strong responders ($\geq 525$ ng/mL ATP) in this assay, were plotted versus time after transplant (see FIG. 6). In the first two months after transplant patients 50% of newly transplanted patients demonstrated immune cell function ATP levels greater than 525 ng/mL and the smallest proportion (~30%) gave ATP levels less than 225 ng/mL. Over the next few months, the proportion of patients showing PHA induced ATP levels <225 ng/mL increased steadily. In the 6-12 month window, no patients reacted in the strong immune response zone ($\geq 525$ ng/mL). The greatest deviation in the low and strong immune responder groups occurred at one year or more after transplant with a slight upswing in the ATP values $\geq 525$ ng/mL at 4 years.

When the proportion of transplant patients with immune response ATP values of $\geq 525$ ng/mL or $\leq 225$/ng/mL are plotted as a function of time, it is not surprising that the greatest number of patients at the extremes of this assay occur in the first months following transplant. In this multi-center trial, 6-12 months appeared to be the point of greatest stability, with no patients with values greater than 525 ng/mL. At later points (>1 year), the proportion of patients with immune response levels $\leq 225$ ng/mL increases. It would appear that once patients have recovered from the trauma of surgery, the effectiveness of immunosuppressive therapy appears to increase over time, despite lower dosing of these dugs. This demonstrates again the importance of the measurement of net immunosuppression, which may indicate that there is additional rationale supporting individualized titration of immunosuppressive therapy. The availability of a direct measure of immune system activity reflecting the potency of therapy in real time allows for a mechanism for drug adjustment. The assay also readily responds to intervention therapies, so that the relative impact of such therapies can now be calibrated, better reflecting a patient's individualized response to these drugs. Ultimately, tailored therapies offer the promise of reducing the long-term morbidities associated with the prolonged use of these drugs without compromising the life of the transplanted organ.

This Example demonstrates that most patients receiving immunosuppressant therapy for prolonged periods of time (greater than one year) show high levels of functional suppression of immunity that does not correlate with the drug level in the blood, which is often at its lowest point.

Example 8

Prediction of Risk of Rejection

Typically, a high dose of an immunosuppressant drug is administered to a patient immediately after transplant surgery, and followed up with additional doses taken daily. Drug monitoring assays and organ function assays, (e.g. creatinine) are performed on a monthly basis. The Cylex™ Immune Cell Function Assay may be performed concurrently to detect changes in the immune response over a period of time. For example, results showing a progression in immune response from the low range ($\leq$225 ng/mL ATP), through the moderate range, and into the strong range ($\geq$525 ng/mL ATP) may serve as a cautionary marker of potential acute rejection, permitting the treating physician to increase drug or introduce a rescue therapy with alternate drug doses, or use in combination with others, or initiate other clinical confirmatory tests (e.g., organ biopsy).

CASE STUDY 1: Induction therapy in transplant recipients leads to a dramatic decrease in the total number of circulating lymphocytes and is intended to reduce acute rejection episodes. This Case Study reports a patient's clinical course as monitored by the Cylex™ Immune Cell Function Assay for 1-year following transplantation (FIG. 7).

A 51 year-old Caucasian male with end-stage renal disease (ESRD) secondary to glomerulonephritis received a living related haplotype-matched kidney. The immunosuppression protocol consisted of induction with anti-CD52 antibodies and maintenance therapy with Sirolimus. The patient's immune response was monitored by the methods of the present invention.

To perform the assay, 200 µl of sodium heparin anticoagulated whole blood was diluted, aliquoted into wells of a 96-well microtiter plate and stimulated overnight with PHA. CD4+ cells were then selected using antibody-coated magnetic particles, washed and lysed to release intracellular ATP. The intensity of the patient's immune response was quantified by measuring the amount of intracellular ATP produced in response to stimulation.

Figure 7:
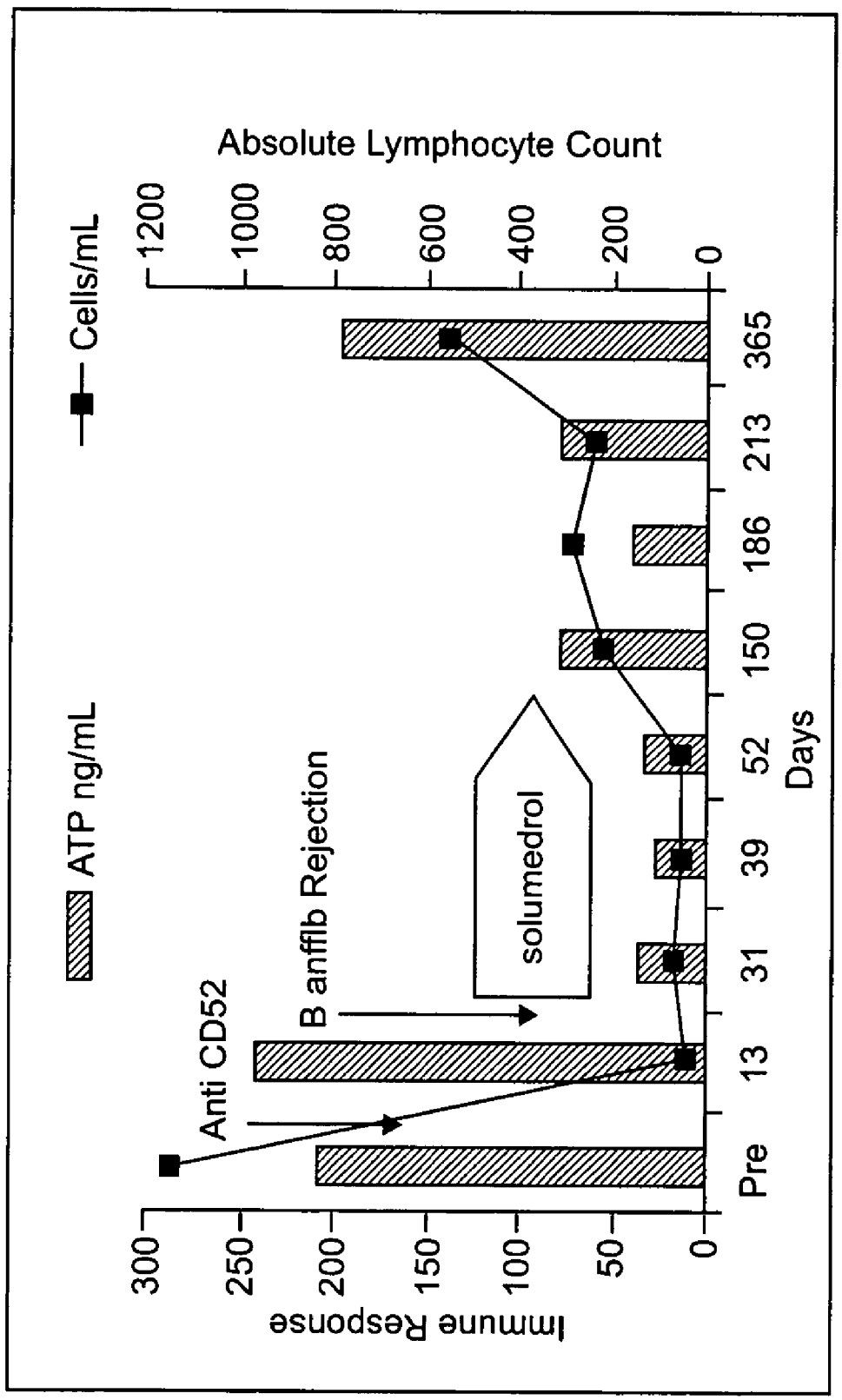
FIG. 7: Case Study 1: Rejection associated with immune cell function despite reduced lymphocyte count following induction therapy. X axis=time (days); left Y axis, immune response (ATP ng/mL); right Y axis=number of lymphocytes.

Treatment with anti-CD52 at transplant led to profound lymphocyte depletion, but the intensity of the post-transplant immune response actually rose from pre-transplant to day 13 see FIG. 7). On day 23, a protocol biopsy revealed a Banff Ib rejection (in the absence of a significant rise in creatinine). Rescue therapy consisted of treatment with solumedrol, a prednisone taper, and Sirolimus. Following this treatment, the patient's Immune Response dropped, indicating an increase in the level of immunosuppression. During this period, Sirolimus drug dosing remained constant, creatinine levels were stable, and lymphocyte counts progressively increased.

Thus, initial induction therapy with anti CD52 led to reduction in the absolute number of circulating lymphocytes. A decrease in the cell number, however, did not translate into suppression of the patient's functional immune response. The immune response level after induction was increased over the pre-transplant value and was associated with rejection. The patient rejected about a week later, despite dramatically lower absolute lymphocyte counts, necessitating modifications to the drug regimen.

The functional responsiveness of circulating lymphocytes is a critical measure in assessing the efficacy of immunosuppressive therapy. This example demonstrates that despite effective lymphodepletion and ongoing immunosuppressive therapy, the lymphocytes remained metabolically active as measured by ATP and as reflected in the ensuing rejection event. ImmuKnow™ provides a valuable adjunct to other clinical parameters in the monitoring of patients post transplant.

Figure 8:
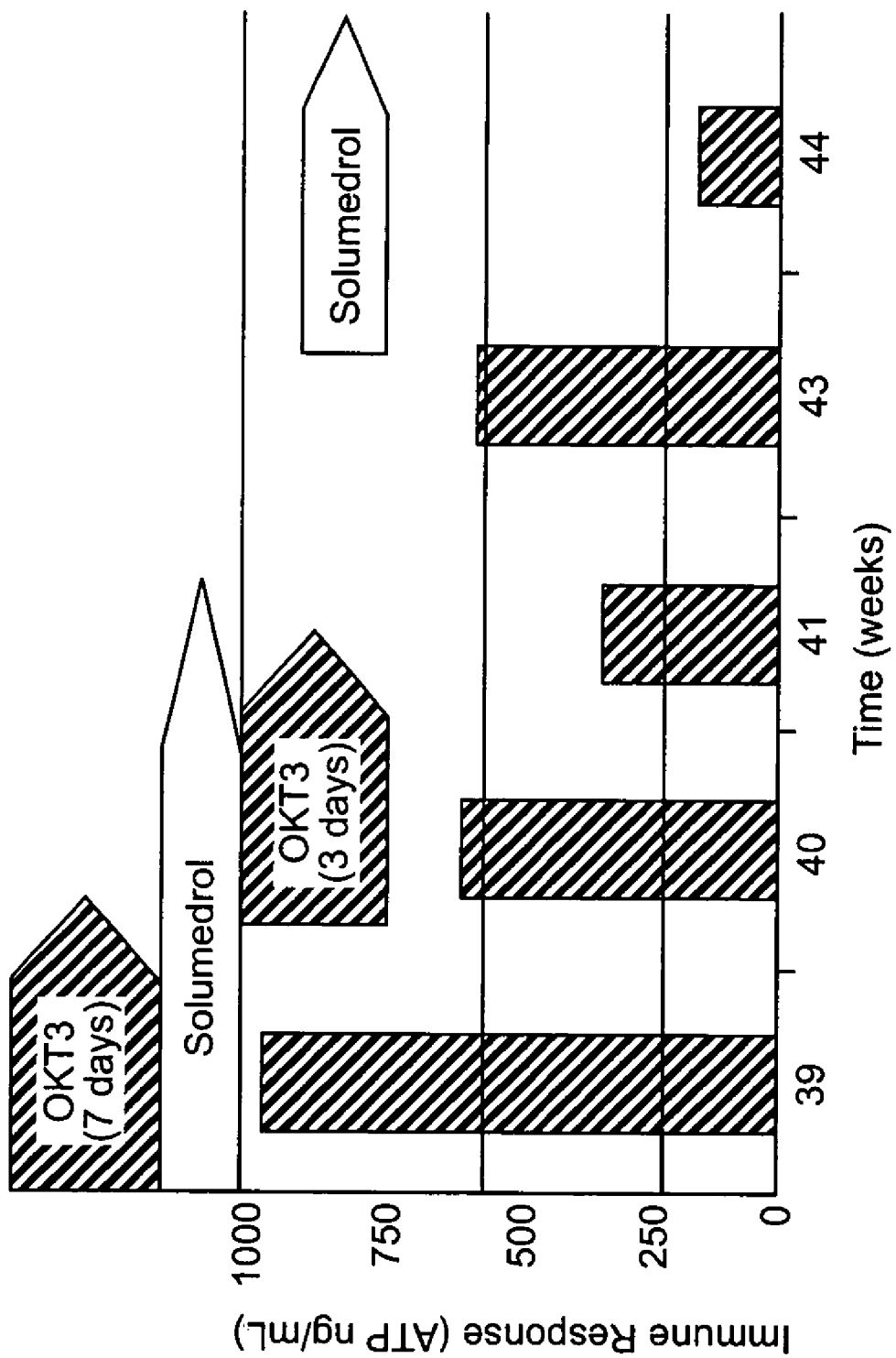
FIG. 8: Case Study 2. Duration of rescue therapy by measurement of immune function. X axis=time in weeks; Y axis=immune response (ATP ng/mL).

CASE STUDY 2. Following rejection, the duration of infusion of monoclonal antibody OKT3 (anti-CD3) (7 to 14 days together with steroids) is based on the degree of rejection as judged by biopsy. Mild to moderate rejections may be given a 7-day treatment while severe rejections warrant a 14-day course. This Case Study describes the clinical course of a multivisceral transplant recipient following treatment for acute rejection with OKT3 and Solumedrol as a function of her immune response (FIG. 8).

A 48-year-old African American female was treated with rATG and infused with donor bone marrow cells prior to receiving an irradiated, multivisceral transplant (small bowel). She received tacrolimus as maintenance therapy.

To perform the Cylex™ Immune Cell Function Assay, 200 µl of sodium heparin anticoagulated whole blood was diluted, aliquoted into wells of a 96-well microtiter plate and stimulated overnight with PHA. CD4+ cells were then selected using antibody-coated magnetic particles, washed and lysed to release intracellular ATP. The intensity of the patient's immune response was quantified by measuring the amount of intracellular ATP produced in response to stimulation. Acute rejection was diagnosed by histopathologic studies of random and endoscopically guided multiple mucosal biopsies. To treat the acute rejection, the patient was given infusions of OKT3 at 10 mg/day in conjunction with IV tacrolimus and solumedrol.

Following a period of stabilization after transplant, tapering of tacrolimus was initated. On week 38, the patient was diagnosed with an acute rejection and infused with OKT3/FK and Solumedrol. On week 39, the immune response as measured by Cylex™ Immune Cell Function Assay was extremely high (ATP=954 ng/mL, see FIG. 8). An additional three-day course of OKT3, instead of 7 days, was given. The immune response dropped by half (ATP=582 ng/mL) and OKT3 and Solumedrol were stopped. The immune response continued to drop through week 41, but climbed to the upper end of the moderate zone two weeks later (week 43). Solumedrol treatment was re-initiated and the immune response dropped significantly (week 44). The patient is currently clinically stable.

Once a recipient's immune system begins to reject an allograft, extremely potent immunosuppressants are required to limit damage or potential loss of the organ. Until recently, the type and dosage of drug(s) and the length of time required to rescue an acute rejection event were based predominately on biopsy results alone. The Cylex™ Immune Cell Function Assay provides a measure of a patient's global immune response that incorporates the aggregate impact of multiple drugs, and the patient's clinical condition. As shown in FIG. 8, initial treatment with OKT3 did not reduce the patient's immune response adequately. A second treatment was needed, but the usual length of time was reduced from 7 to 3 days. By supplementing maintenance therapy of tacrolimus with steroids, this patient is now clinically stable with an intact, functional and rejection free organ. The Cylex™ immune function assay ImmuKnow™ assay gauged the effectiveness of rescue therapy and helped limit the amount of immunosuppressants administered to this patient.

The Cylex™ Immune Cell Function Assay provides a measure of the aggregate impact of immunosupressive therapy, allowing the physician to better individualize a patient's course of therapy.

Example 9

Prediction of Risk of Infection

A dose of an immunosuppressant drug such as Rapamycin is reduced over time according to a protocol during post-liver-transplant therapy. Therapeutic drug monitoring assays are performed monthly which indicate that drug trough levels are within expected range.

The Cylex™ assay performed at the same time detects an unexpected continued decrease in the immune response over an extended period of time from the moderate range (>225 ng/mL ATP, <525 ng/mL ATP) to the low range (≦225 ng/mL ATP). Further monitoring indicates a continuing decrease over time. These results serve as an indication of potential risk of opportunistic infection due to over medication, and allows the physician to reduce drug doses or initiate other clinical confirmatory tests (e.g., organ biopsy or organ function analysis). See case studies 1 and 2.

Example 10

Prediction of Favorable Outcome

An immunosuppressive drug such as Cyclosporin is administered over an extended period of time after heart transplant surgery. During this time the drug is weaned in order to avoid long-term toxic effects. Drug level monitoring reflects this decrease, however the Cylex™ immune function assay performed concurrently indicates that the patient's immune response remains within the moderate range (>225 ng/mL ATP, <525 ng/mL ATP). This indicates that there is little likelihood of rejection or damage to the organ due to toxicity.

REFERENCES

1. UNOS, 2001 International Transplant Directory. *Transplant News*; Transplant Communications Inc., Fresno, Calif.
2. Rovira, P, Mascarell, L and Truffa-Bachi, P. The Impact of Immune Suppressive Drugs on the Analysis of T Cell Activation. *Current Medicinal Chem*. 2000(7):673-692.
3. Venkataraman, R, Shaw, L M, Sarkozi, L, Mullins, R, Pirsch, J, et al. Clinical Utility of Monitoring Tacrolimus Blood Concentrations in Liver Transplant Patients. *J Clin. Pharm.* 2001; 41:542-551.
4. Ahmed, M, Vankataraman, R, Logar, A J, Rao, A S, Bartley, G P, Robert, K, Dodson, F S, Shapiro, R, Fung J J and Zeevi, A. Quantitation of Immunosuppression by Tacrolimus Using Flow Cytometric Analysis of Interleukin-2 and Y-Interferon and Inhibition in CD8⁻ and CD8+ Peripheral Blood T Cells, *Therapeutic Drug Monitoring* 2001; 23(4): 354-362.
5. Weir, M L Methods for Measurement of Lymphocyte Function. U.S. Pat. No. 5,773,232: 1998.
6. Hawkins, D M Diagnostics for Conformity of Paired Quantitative Measurements, In: *Statistics in Medicine*: 2001
7. Rocke, D M and Lorenzato, S. A Two-Component Model for Measurement Error in Analytical Chemistry, *Technometrics*, 1995; 37, 176-184.
8. Buttgereit, F, Burmester, G-R, Brand, M D. Bioenergetics of Immune Functions. Fundamental and Therapeutic Aspects. *Immunol. Today* 2000; 21:192-199.
9. Britz, J A, Sottong, P and Kowalski, R. In vitro CMI™: Rapid Assay for Measuring Cell-Mediated Immunity. In: *Luminescence Biotechnology Instruments and Applications*. Ed. Van Dyke, Van Dyke and Woodfork, CRC Press. 2002; p.331-344.
10. Sottong, P R, Rosebrock, J A, Britz, J A and Kramer, T R. Measurement of T-lymphocyte Responses in Whole Blood Cultures Using Newly Synthesized DNA and ATP. *Clinical and Diagnostic Laboratory Immunology*, 2000; Vol. 7:307-311.
11. Halsey, J F, New Methods, Clinical Applications of T Cell Functional Assays. *Advance/Laboratory*. October 2001; p67-72.
12. Schulick, R D, Weir, M B, Miller, M W, Cohen, D J, Bernas, B L and Shearer, G M. Longitudinal Study of In Vitro CD4+ Helper Cell Function in Recently Transplanted Renal Allograft Patients Undergoing Tapering of their Immunosuppressive Drugs, *Transplantation*. 1993; Vol. 56 No. 3:590-596.
13. Danovitch, G M. Current Immunosuppressive Regimes in Organ Transplantation. *Kidney International*. 2001. Vol. 59:p388-402.
14. Danovitch, G M. Immunosuppressive medications for renal transplantation: A multiplechoice question. International Society of Nephrology. *Kidney International*. 2001 Vol. 59:388-402.
15. Jusko, W J, Thomson, A W, et al. Consensus Document: Therapeutic Monitoring of Tacrolimus (FK-506). *Ther. Drug Monitoring*; 1995; 17:606-614.
16. Burdick, J F, Shinozuka, N. Immune Monitoring for Transplant Recipients. In: Kidney Transplant & Rejection: Diagnosis and Treatment. Ed. Racusen, Dekker, Marcel Inc. 1998; p563-575.
17. Zeevi, A, Bentlejewski, C, Spichty, K, Griffith, B, Abu-Elmagd, K, Hooper, N, Kowalski, R, and Fung, J. Post Transplant Immune Monitoring—ATP Based Assay for T Cell activation. Presented at 2001 *Clinical Histocompatibility Workshop*, Honolulu, Hi.
18. Fletcher, M A, Urban, R G, Asthana, D., Walling, J., Friedlander, A., Page, J. B. Lymphocyte Proliferation, In: Rose, N. R., et al (eds.), *Manual of Clinical Laboratory Immunology*: 5th Ed. American Society for Microbiology, 1997; p313-319. Washington, D.C.
19. Liu, J, Farmer, J D, Lane, W S, et al. Calcineurin is a common target of cyclophilincyclosporin A and FKBP-FK506 complexes. 1991. *Cell* 66:807-901.

20. Karlsson H, DePierre J W, Nassberger, L. Energy Levels in Resting and Mitogen-Stimulated Human Lymphocytes During Treatment with FK506 or Cyclosporin A In Vitro. 1997. *Biochim Biophys Acta*. 1319(2-3):301-310.

21. Horigome, A, Hirano T, Oka, K. Tacrolimus-Induced Apoptosis and its Prevention by Interleukins in Mitogen-Activated Human Peripheral-Blood Mononuclear Cells. 1998. *Immunopharmacology* 39(1):21-30.

22. Kahan, B D, M. Welsh, L. Rutzky, et al. The Ability of Pretransplant Test-Dose Pharmacokinetic Proflies to Reduce Early Adverse Events after Renal Transplantation. Transplantation 1992; 53:345.

23. Butkus, D E, Meydrech, E F, Raju, S S. Racial Differences in the Survival of Cadaveric Renal Allografts. Overriding Effects of HLA Matching and Socioeconomic Factors. *N. Engl. J. Med*. 1992. 327.-840-845.

24. Van Buren, D H. Renal Transplantation Outcomes in African-American Patients. *Transplant Immunol. Lett*. 1999. 15:61-11.

25. Nagashima, N, Watanabe, T, Nakamura, M, Shalabi, A, Burdick, J F. Decreased Effect of Iimmunosuppression on Immunocompetence in African-Americans After Kidney and Liver Transplantation, *Clin. Transplantation*. 2001. 15:111-115.

26. Halsey, personal communication.

While the invention has been described in terms of its preferred embodiments, those skilled in the art will recognize that the invention can be practiced with modification within the spirit and scope of the appended claims. Accordingly, the present invention should not be limited to the embodiments as described above, but should further include all modifications and equivalents thereof within the spirit and scope of the description provided herein.

We claim:

1. A method of treating a patient that has received a transplant and is being provided with one or more immunosuppressive drugs, comprising the steps of:
    a) determining a value of an immune response for said patient which reflects activation of CD4 lymphocytes in a whole blood sample stimulated by exposure to phytohemagglutinin (PHA) measured in terms of adenosine triphosphate (ATP) weight in volume of cell lysate of cells isolated from said whole blood sample by immunoselection for CD4 lymphocytes;
    b) comparing said value with values in a reference set comprising ranges of values of immunological responses for CD4 lymphocytes, wherein said reference set comprises low, moderate and strong ranges of values, wherein values of said low range are less than or equal to 225 nanograms of ATP per mL, values of said moderate range are greater than 225 nanograms of ATP per mL and less than 525 nanograms of ATP per mL, and values of said strong range are equal to or greater than 525 nanograms of ATP per mL; and
    c) based on a comparison obtained from said comparing step, predicting said patient is at risk of rejection of a transplanted organ if said value compared in said comparing step is in said strong range or ascertaining said patient is at risk of being overmedicated with said one or more immunosuppressive drugs if said value compared in said comparing step is in said weak range.

2. The method of claim 1 wherein said patient is a recipient of a transplant selected from the group consisting of heart, lungs, kidney, pancreas, liver, small bowel, skin, tissues and bone marrow.

3. The method of claim 1 wherein steps (a)-(c) are performed multiple times.

4. The method of claim 3 further comprising the step of
    d) adjusting a therapeutic regimen for said patient if said patient is at risk of rejection of said transplanted organ or is at risk of being overmedicated.

5. The method of claim 4 wherein said adjusting step includes increasing or decreasing quantities of an immunosuppressive drug being provided to said patient.

6. The method of claim 4 wherein said adjusting step includes changing medication provided to said patient.

7. The method of claim 1 wherein steps (a)-(c) are performed multiple times over a period of years.

8. A method of treating a patient that has received a transplant and is being provided with one or more immunosuppressive drugs, comprising the steps of:
    a) determining, at a first and a second time, a value of an immune response for said patient which reflects activation of CD4 lymphocytes in a whole blood sample stimulated by exposure to phytohemagglutinin (PHA) measured in terms of adenosine triphosphate (ATP) weight in volume of cell lysate of cells isolated from said whole blood sample by immunoselection for CD4 lymphocytes;
    b) comparing said value determined at said first time with said value determined at said second time, and if there is a decrease of at least about 50 ng/ml ATP, determining that said patient is at risk of being overmedicated with said one or more immunosuppressive drugs; and
    c) if said patient is at risk of being overmedicated, adjusting a therapeutic regimen for said patient.

9. A method of treating a patient that has received a transplant and is being provided with one or more immunosuppressive drugs, comprising the steps of:
    a) determining, at a first and a second time, a value of an immune response for said patient which reflects activation of CD4 lymphocytes in a whole blood sample stimulated by exposure to phytohemagglutinin (PHA) measured in terms of adenosine triphosphate (ATP) weight in volume of cell lysate of cells isolated from said whole blood sample by immunoselection for CD4 lymphocytes;
    b) comparing said value determined at said first time with said value determined at said second time, and if there is an increase of at least about 50 ng/ml ATP, determining that said patient is at risk of rejection; and
    c) if said patient is at risk of rejection, adjusting a therapeutic regimen for said patient.

* * * * *